United States Patent
Vetrecin et al.

(10) Patent No.: US 8,324,292 B2
(45) Date of Patent: Dec. 4, 2012

(54) MEDICALLY ACCEPTABLE FORMULATION OF A DIISOCYANATE TERMINATED MACROMER FOR USE AS AN INTERNAL ADHESIVE OR SEALANT

(75) Inventors: Robert B. Vetrecin, Stewartsville, NJ (US); Elizabeth Vailhe, Hillsborough, NJ (US); Robert W. Van Holten, Flemington, NJ (US)

(73) Assignee: Ethicon, Inc., Somerville, NJ (US)

( * ) Notice: Subject to any disclaimer, the term of this patent is extended or adjusted under 35 U.S.C. 154(b) by 76 days.

(21) Appl. No.: 12/040,211

(22) Filed: Feb. 29, 2008

(65) Prior Publication Data

US 2009/0221731 A1    Sep. 3, 2009

(51) Int. Cl.
 A61L 24/04    (2006.01)
 A61F 2/00    (2006.01)
 C08G 18/70    (2006.01)
 C08G 18/72    (2006.01)
 C08G 18/77    (2006.01)
 C07C 265/12    (2006.01)

(52) U.S. Cl. ........ 523/118; 523/111; 523/113; 424/423; 528/44; 528/59; 528/67; 560/330

(58) Field of Classification Search ................ 523/118, 523/111, 113; 424/423; 528/44, 59, 67; 560/330, 331
See application file for complete search history.

(56) References Cited

U.S. PATENT DOCUMENTS

| | | |
|---|---|---|
| 4,740,534 A | 4/1988 | Matsuda et al. |
| 4,804,691 A | 2/1989 | English et al. |
| 4,806,614 A | 2/1989 | Matsuda et al. |
| 4,829,099 A | 5/1989 | Fuller et al. |
| 4,938,763 A | 7/1990 | Dunn et al. |
| 4,994,542 A | 2/1991 | Matsuda et al. |
| 5,035,893 A | 7/1991 | Shioya et al. |
| 5,118,779 A | 6/1992 | Szycher |
| 5,173,301 A | 12/1992 | Itoh et al. |
| 5,175,229 A | 12/1992 | Braatz et al. |
| 5,192,536 A | 3/1993 | Huprich |
| 5,270,358 A | 12/1993 | Asmus et al. |
| 5,457,141 A | 10/1995 | Matsuda et al. |
| 5,486,547 A | 1/1996 | Matsuda et al. |
| 5,584,801 A | 12/1996 | Kuroyanagi et al. |
| 5,707,647 A | 1/1998 | Dunn et al. |
| 5,717,030 A | 2/1998 | Dunn et al. |
| 5,804,213 A | 9/1998 | Rolf |
| 5,844,013 A | 12/1998 | Kenndoff et al. |
| 5,914,125 A | 6/1999 | Andrews et al. |
| 6,155,265 A | 12/2000 | Hammerslag |
| 6,210,441 B1 | 4/2001 | Flodin |
| 6,375,966 B1 | 4/2002 | Maleeny et al. |

(Continued)

FOREIGN PATENT DOCUMENTS

EP    0328585    9/1994

(Continued)

OTHER PUBLICATIONS

NTC Project: M01-CR01; p. 1-10; National Textile Center Annual Report: Nov. 2002.*

(Continued)

*Primary Examiner* — Michael Pepitone
(74) *Attorney, Agent, or Firm* — David R. Crichton

(57) ABSTRACT

A medically acceptable formulation comprising a diisocyanate terminated macromer or mixture thereof, and an oxidized cellulose.

6 Claims, 4 Drawing Sheets

U.S. PATENT DOCUMENTS

| | | | |
|---|---|---|---|
| 6,524,327 B1 | 2/2003 | Spacek | |
| 6,702,731 B2 * | 3/2004 | Milbocker | 600/30 |
| 6,894,140 B2 | 5/2005 | Roby | |
| 7,728,097 B2 | 6/2010 | Fitz et al. | |
| 2002/0049503 A1 | 4/2002 | Milbocker | |
| 2004/0078090 A1 * | 4/2004 | Binette et al. | 623/23.76 |
| 2004/0115229 A1 | 6/2004 | Roby | |
| 2004/0170597 A1 | 9/2004 | Beckman et al. | |
| 2004/0243042 A1 | 12/2004 | Lipman | |
| 2005/0129733 A1 * | 6/2005 | Milbocker et al. | 424/423 |
| 2006/0147492 A1 * | 7/2006 | Hunter et al. | 424/426 |
| 2006/0153796 A1 | 7/2006 | Fitz | |
| 2006/0172000 A1 * | 8/2006 | Cullen et al. | 424/445 |
| 2006/0280720 A1 | 12/2006 | Fitz et al. | |
| 2006/0281874 A1 | 12/2006 | Fitz et al. | |
| 2007/0154530 A1 * | 7/2007 | Cullen et al. | 424/445 |
| 2007/0167617 A1 | 7/2007 | Fitz et al. | |
| 2007/0276121 A1 | 11/2007 | Westergom et al. | |
| 2008/0125811 A1 * | 5/2008 | Bettuchi | 606/214 |
| 2008/0226691 A1 * | 9/2008 | Armitage et al. | 424/423 |

FOREIGN PATENT DOCUMENTS

| | | |
|---|---|---|
| WO | WO 2006/076291 | 7/2006 |
| WO | WO 2006/076291 A1 | 7/2006 |
| WO | WO 2007/089430 | 8/2007 |
| WO | WO 2008/019383 | 2/2008 |

OTHER PUBLICATIONS

"Polymeric Biomaterials", $2^{nd}$ Ed., Marcel Dekker Inc., (2002) pp. 716.

Organic Chemistry J. McMurry, 2nd ed., Brooks/Cole Publishing Company (1988) pp. 1129.

International Search Report re: PCT/US2009/035052 dated Apr. 12, 2010.

International Search Report re: PCT/US2010/29010 dated May 4, 2010.

* cited by examiner (Ia)

(Ib)

MEDICALLY ACCEPTABLE FORMULATION OF A DIISOCYANATE TERMINATED MACROMER FOR USE AS AN INTERNAL ADHESIVE OR SEALANT

RELATED APPLICATION

This application is related to U.S. application Ser. No. 11/772,401, filed on 2 Jul. 2007; U.S. application Ser. No. 11/333,057, filed on Jan. 17, 2006; and U.S. application Ser. No. 11/476,512, filed on 28 Jun. 2006, which is continuation-in-part of U.S. application Ser. No. 11/032,332, filed on Jan. 10, 2005.

FIELD OF THE INVENTION

Described herein are novel polyisocyanate macromers or mixture thereof and the use thereof to form an internal adhesive or sealant for use in cardiovascular, peripheral-vascular, cardio-thoracic, gynecological, neuro- and general abdominal surgeries. More particularly, the macromers or mixture thereof or a formulation thereof polymerizes in the human body to form an elastic gel that is biocompatible and that degrades into products that are non-toxic and biocompatible. Additionally, the degradation products are water soluble, allowing for the degradation products to be eliminated from the human body as waste products.

BACKGROUND OF THE INVENTION

Generally, the key requirements of a tissue adhesive are:
(1) In use, the adhesive must mimic the mechanical performance of the undamaged tissue;
(2) The adhesive should provide sufficient tack for "primary" fixation with the opportunity for manipulation and re-alignment prior to setting strongly;
(3) Any exothermic process involved in the curing of the adhesive should not damage the surrounding tissue;
(4) The adhesive must not elicit any toxic response by the surrounding healthy tissue and should facilitate the re-growth of new tissue where possible;
(5) The adhesive should not liberate harmful degradation products;
(6) The adhesive should degrade, and as it does so, it should be replaced by new tissue with minimal scarring; and
(7) Any biodegradation products should not accumulate in the body but should be eliminated naturally either by excretion or incorporation into the natural biochemical cycle.
["Polymeric Biomaterials", $2^{nd}$ Ed., Marcel Dekker Inc., (2002) pp. 716]

It is well known in the art that diisocyanate monomers may be used to form polymeric adhesives. However, many of the diisocyanate monomers that are commercially available are small molecule diisocyanate monomers that present toxicity and sensitization hazards and that polymerize to form products having toxic degradation products, for instance, aromatic amines. As such, commercially available small molecule diisocyanate monomers are unsuitable for human use as an internal adhesive or sealant.

Metabolically acceptable polyisocyanate monomers are described in U.S. Pat. No. 4,829,099. More specifically, this reference describes an aromatic benzoyl isocyanate terminated monomer, having glycolic acid residues and polyethyleneglycol residues, in formula "I, Preferred". This reference indicates that the resultant polymer will degrade ultimately to metabolically acceptable products, including p-aminobenzoic acid, polyethylene glycol and glycolic acid. Although the resultant polymer in principal could degrade into the aforementioned compounds, it is believed that only the glycolic acid residues would hydrolyse in vivo, resulting in a mixture of water-soluble and water insoluble fragments. The water-soluble fragments would be eliminated naturally by excretion from the body. However, the water insoluble fragments would not be eliminated naturally, resulting in the undesirable accumulation of the water insoluble fragments in the body.

Polyester-urethane-urea block copolymers prepared from commercially available small molecular diisocyanates, i.e. tolylene diisocyanate (TDI), diphenylmethane-4,4'-diisocyanate (MDI), and hexamethylene diisocyanate (HMDI), are described in U.S. Pat. No. 6,210,441. However, these copolymers would be unsuitable for use as a surgical adhesive or sealant, since the copolymers are already polymerized, i.e., already cured, and would not provide sufficient opportunity for manipulation and re-alignment. Moreover, such copolymers are not believed to mimic the mechanical performance of undamaged tissue.

Therefore, it is desirable to have a monomer based internal adhesive or sealant formulation that is capable of polymerizing in vivo to form an internal adhesive or sealant, in order to provide an opportunity for manipulation and re-alignment. Specifically, it is desirable that the adhesive or sealant formulation fills internal cavities and voids, penetrating and conforming to the interstices and pores of the tissue, prior to curing or setting.

Additionally, it is desirable to have a monomer based internal adhesive or sealant formulation that polymerizes in vivo, where the monomer, the formulation thereof, and the resultant polymer are biocompatible. The resultant polymer should also be biodegradable.

Finally, it is desirable that the degradation products of the resultant polymer be both biocompatible and water soluble, so that the degradation products are completely eliminated from the human body as waste products.

SUMMARY OF THE INVENTION

Novel macromers or a mixture thereof are described herein, comprising benzoyl isocyanate terminal moieties containing at least one hard segment urea group and at least two residues of a soft segment water-soluble polymer having a molecular weight ranging from 80 to 10,000 adjacent to the carbonyl group of the benzoyl isocyanate moieties, thereby forming at least two ester linkages in the macromer.

DEFINITIONS

Unless defined otherwise, all technical and scientific terms used herein have the same meaning as is commonly understood by one of skill in the art to which this invention belongs. All patents and publications mentioned herein are incorporated by reference.

"Biocompatible" as used herein refers to a material that, once implanted, does not interfere significantly with wound healing and/or tissue regeneration, and does not cause any significant metabolic disturbance.

"Biodegradable" and "bioabsorbable" as used herein refer to a material that is broken down spontaneously and/or by the mammalian body into components, which are consumed or eliminated in such a manner as not to interfere significantly with wound healing and/or tissue regeneration, and without causing any significant metabolic disturbance.

"Water-soluble polymer" as used herein refers to a polymer, which dissolves in water, forming transparent solutions under ambient conditions (e.g. body temperature).

"Polyisocyanate" as used herein refers to a compound with two or more isocyanate groups.

"Urethane linkage" as used herein refers to a residue derived from a urethane moiety and having a carbonyl-containing functional group in which the carbonyl carbon is bound both to an ether oxygen and to an amine nitrogen:

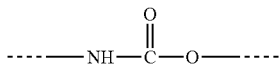

["Organic Chemistry", J. McMurry, $2^{nd}$ ed., Brooks/Cole Publishing Company, (1988), pp 1129].

"Urea linkage" as used herein refers to a residue derived from a moiety having a carbonyl-containing functional group in which the carbonyl carbon is bound to identical units of amine nitrogen:

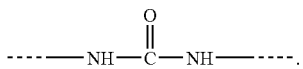

["Nomenclature of Organic Chemistry", Pergamon Press, Oxford, (1979)].

"Hard segment" as used herein refers to the portion of the repeating unit that imparts tensile strength and rigidity to the polymer.

"Soft segment" as used herein refers to the portion of the repeating unit that is typically modified to control elasticity, pliability and similar properties to the polymer

DETAILED DESCRIPTION OF THE INVENTION

Figure 1:
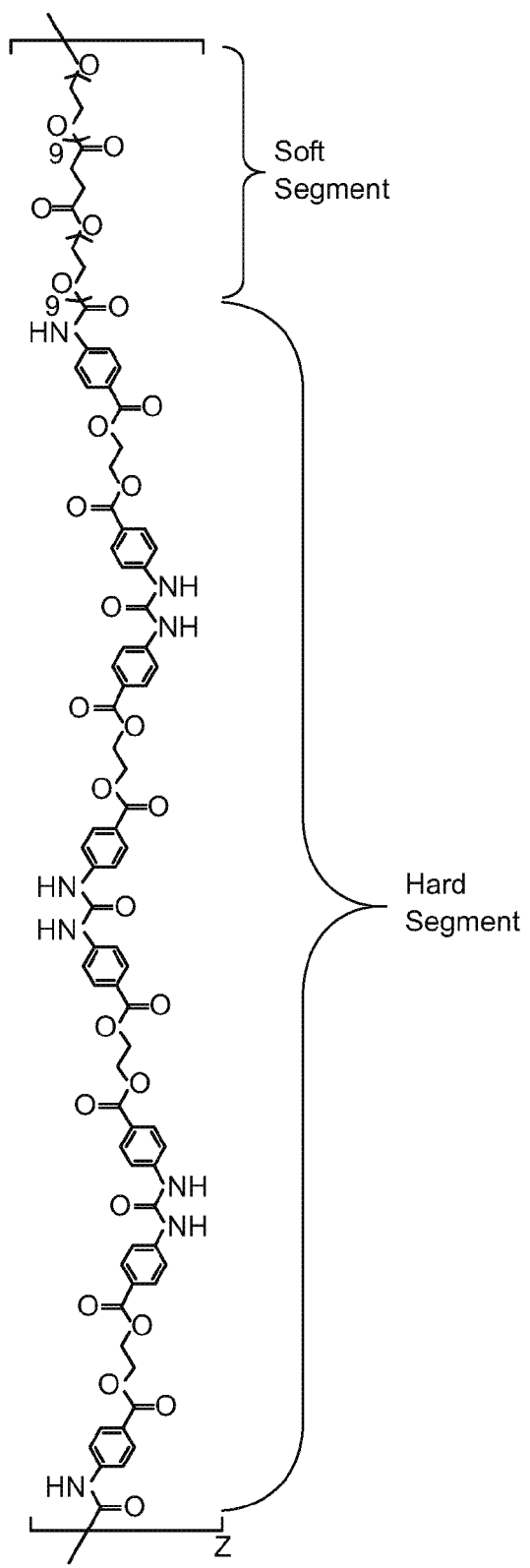
FIG. 1 shows a polyurethane structure having "hard" and "soft" segments.

As described above, a monomer based internal adhesive or sealant formulation that is capable of polymerizing in vivo to form an internal adhesive or sealant, should wet the tissue to which it is applied, penetrating and conforming to the interstices and pores of the tissue, prior to curing or setting. Additionally, the monomer, the formulation thereof, and the resultant polymer should be biocompatible.

The monomer and the formulation thereof described herein are suitable for internal applications, since neither the monomer, the formulation thereof nor the resultant polymer metabolizes in the human body to form toxic products.

Additionally, the monomer and the formulation thereof polymerize to form a biocompatible polymer upon contact with water or body fluids. The biocompatible polymer then degrades in vivo to form degradation products that are both biocompatible and water soluble, which are then eliminated from the human body as waste products.

The monomer and the formulation thereof have multiple medical applications and may be used in many types of surgery, including, but not limited to, cardiovascular, peripheral-vascular, cardio-thoracic, gynecological, neuro- and general abdominal surgery.

For example, the monomer and the formulation thereof may be used as an internal surgical adhesive in orthopedic procedures such as anterior cruciate ligament repair, meniscal tear repair (or as a hydrogel for the replacement of the meniscus), posterior capsule reconstruction, rotator cuff repair, and as a bone adhesive. It could also be used as an adhesive for lung volume reduction, patch fixation, subcutaneous tissue repair, and aortic dissection. In particular, it can be used as stomach adhesive for stomach volume reduction, and as adhesive for mesh fixation for hernia repair, drain fixation, valve attachment, attachment for adhesion prevention films, attachment of tissue to tissue (e.g. synthetic or biologic tissue scaffold to tissue, bioengineered tissue to tissue), tissue to device (e.g. mesh, clip, film) and device to device.

Second, the monomer and the formulation thereof may be used for subcutaneous tissue repair and for seroma prevention in procedures such as mastectomy, breast reconstruction & augmentation, reconstructive or cosmetic abdominoplasty and liposuction, face lift, C-section, hysterectomy in obese patients, orthopedic on thigh region, incisional hernia repair, lipoma excision, traumatic lesions, fistula treatment, graft fixation, and nerve repair.

Third, the monomer and the formulation thereof may be used as a sealant to attach and seal dural patch products, bile duct, bile leaks in liver bed, bladder leaks, bone graft, burn graft dressing and liquid occlusive dressing. As a sealant, it can be coated on tissue, device, and tissue-device interface and it can be used as dural-cranial sealant, dural-spine sealant, cardio/peripheral vascular sealant, GI sealant (e.g. esophagus, intestine, large organ, pancreas, stomach, and gastric ulcer), lung sealant, soft organ sealant (e.g. liver, spleen, pancreas), bonewax substitute, tumor sealant, staple/glue combination, sealant/hemostats combination, urethra sealant. It can be used in procedures including, but not limited to, gastric bypass, parenchymatous organs resection, tracheostomy, ulcerative colitis diverticulosis, radical prostatectomy, sinus reconstruction, sternotomy, choledochoduodenostomy, and gallbladder (liver) bed sealing, and cholecystectomy.

Fourth, the monomer and the formulation thereof may be used as a filler or a periurethral bulking agent in procedures including, but not limited, to dead space removal in reconstructive and cosmetic surgeries, (e.g. plastic/cosmetic/reconstructive, face/facial defect, or void filling), urinary incontinence and other gynecologic procedures, anal fissure/ fistula, catheter injection into myocardium for treating congestive heart failure, nuclear augmentation, pancreatic/ hepatic cyst/fistula obliteration, and pediatric esophogeal fistula.

Fifth, the monomer and the formulation thereof may be used as a matrix for tissue engineering (e.g. tissue scaffolds, delivery matrix for cells, delivery matrix for brachytherapy (radiation therapy) agents, delivery matrix for growth factors, injection matrix for in situ-forming empty cell scaffold, injection matrix for scaffold for delivery of stem cells, cell lysate, or other biologics, bioactives, pharmaceuticals, and neutraceuticals, localization matrix for chemotherapy, and localization matrix for contrast agent.

Sixth, the monomer and the formulation thereof may be used as an adhesion prevention barrier in procedures such as cardiac, open chest, general surgery, obstetrics and gynecological surgeries, orthopedic surgeries, and spine (e.g. artificial disk).

Seventh, the monomer and the formulation thereof may be used as an occluding material for embolization (e.g. GI Fistula, cerebral/vascular occlusive brain aneurism, tubal occlusion, and varicose vein occlusion).

Macromer

In polyurethane chemistry, the hard segment is a term used to describe the contribution of the cured polyurethane chain from the starting polyisocyanate, and the soft segment is a term used to describe the contribution of the cured polyurethane chain from the polyol, polyamine etc. The soft segment is named such because this portion of the repeating unit is typically modified to control elasticity, pliability and similar properties of the polymer. The hard segment is typically the portion of the repeating unit that imparts tensile strength and rigidity to the polymer. Increasing or decreasing the weight % contribution of either segment to the polymer repeating unit will affect the final properties of the film, such as flexibility, strength, etc. A non-limiting example to modify the strength of polyurethanes is a formulation containing a molar excess of polyisocyanate to polyol. When cured, the polyurethane will contain hard segments of repeating urea groups, shown in FIG. 1.

The monomer described herein is a biocompatible polyisocyanate macromer, terminating with benzoyl isocyanate groups and having the structural formula I:

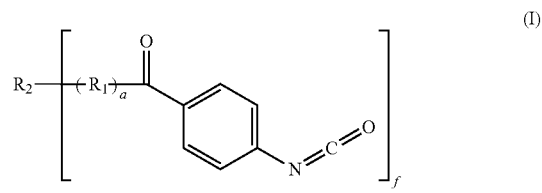

where $R_1$ is an organic residue containing a urethane linkage that is attached to $R_2$ when the value of "a" is one or more, and preferably one to five. The value of f represents the number of end groups on the macromer. When f=2, formula Ia (FIG. 2) represents a linear macromer, when f is three or more, formula Ib (FIG. 3) represents a branched macromer.

An example of $R_1$ when "a" is one or more is shown below:

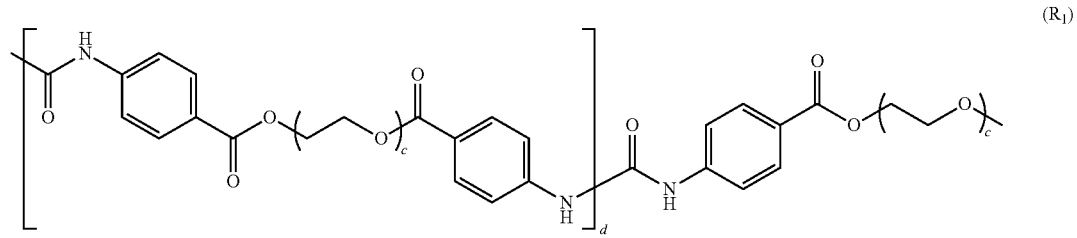

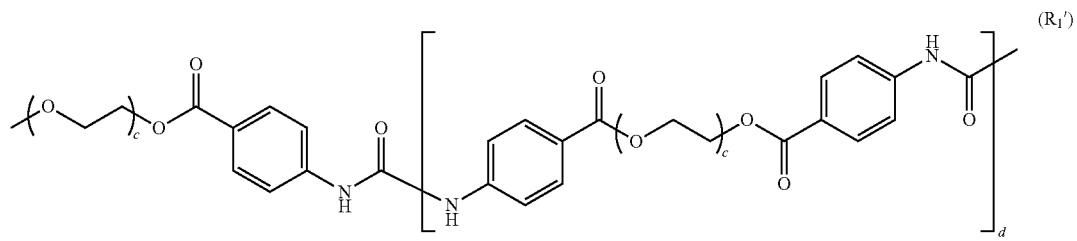

where d is the mean number of repeating "hard" segments within the isocyanate macromer and $0 \leq d \leq 5$; the ethylene oxide portion of $R_1$ may be linear or branched, and c may range from 1 to 100, and preferably from 1 to 10. The number of urea groups is represented by d. An increase in d correlates to an increase in the number of urea groups, which leads to greater strength and rigidity of the polyurethane. In cases where the number of macromer end groups in (I) is greater than 2, it is possible for d to be a fraction. The equation for determining d is shown in equation 1:

$$d = \frac{(d' + d'' + d''' \ldots + d_n)}{\sum f_n}$$

$R_1'$ is the mirror image of $R_1$. A non-limiting example where d is not an integer is shown in the formula (II) shown below.

(III)
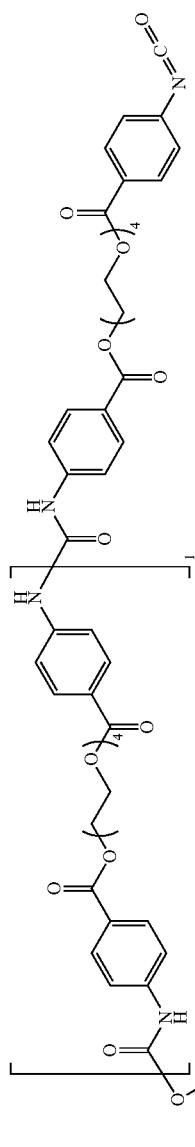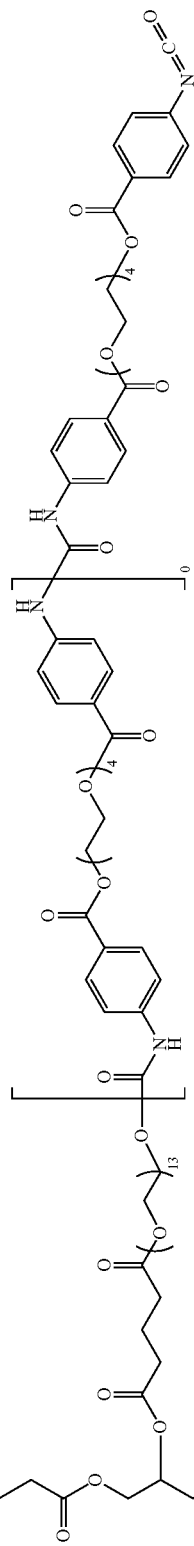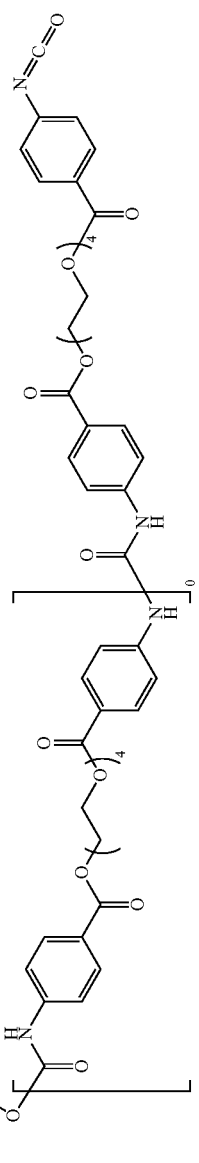

In this structure (II), where $d=d'+d''+d'''=1+0+0=1$ and $f=3$, the average value of $d=0.3333$ per $f$ number of groups.

The general structure of $R_2$ in formula I is the following:

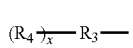 (R$_2$)

where $R_2$ in formula I has hydrolysable ester linkages that are biodegradable in vivo; $R_3$ may be residue of a water soluble polymer, including but not limited to a residue of a polyalkylene glycol such as polyethylene glycol, a polyalkylene oxide, polyvinylpyrolidone, poly(vinyl alcohol), poly(vinyl methyl ether), polyhydroxymethyl methacrylate, a polyacrylic acid polymer and copolymer, polyoxazoline, polyphosphazine, polyacrylamide, a polypeptide, or the water-soluble derivatives of any of the above, that is capable of forming ester linkages together with $R_4$, and urethane linkages together with $R_1$ when "a" is one or more. Further, $R_3$ may be linear or branched. When $R_3$ is a polyethylene glycol residue,

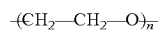

and "a" is one or more, n should be sufficiently large to render the degradation product IV (shown below) water soluble. For example, n may range from 2 to 250, preferably from 5 to 100, and more preferably is 5 to 25. The molecular weight of $R_3$ may range from 80 to 10,000, preferably 200 to 6000, and more preferably 200 to 4000. These residues of water-soluble polymer must be coupled into the macromer in the $R_3$ position and are critical to the solubility of the degradation products, as will be discussed in more detail below.

$R_4$ may be an organic residue capable of having "X" carboxylate end-groups where $2<X<6$. For example, $R_4$ may be derived from linear diacids, such as diglycolic acid, malonic acid, glutaric acid, succinic acid, adipic acid, or carboxylic acid terminated-polyalkyleneglycols such as polyalkylene glycol dicarboxylates.

If $R_4$ is an aliphatic dicarboxylate:

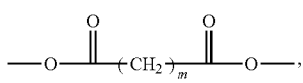

m may range from 1 to 10. The selection of m is based on two factors: biocompatibility and solubility of degradation products. If m is 0, the diacid hydrolytic degradation product of the macromer is too acidic, thus detrimental to biocompatibility of the composition. If m is too large, the diacid degradation product will no longer be water-soluble.

Alternatively, $R_4$ may be derived from a branched acid such as tricarballylic acid, citric acid, or tartaric acid or the glutaric anhydride derivative thereof. Alternately, $R_4$ may be derived from any of the aforementioned acids, carboxylic acid terminated-polyalkyleneglycols or glutaric anhydride derivative, resulting in a compound with carboxylate end-groups. Additional examples of $R_4$ are shown below:

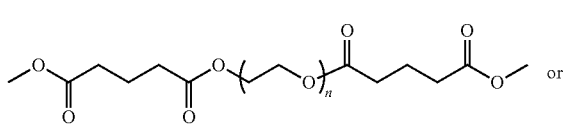 or

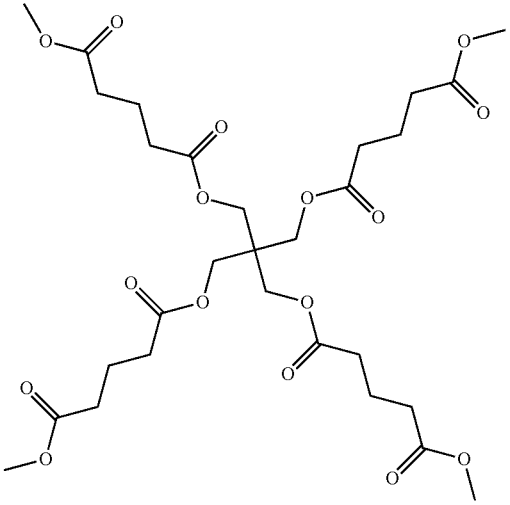

Alternately, $R_2$ may be formed from any carbonyl-containing moiety via synthetic routes (including but not limited to trans-esterification, acid halide-alcohol condensation, acid-alcohol condensation) resulting in ester linkages to $R_3$.

Examples of $R_2$ include but are not limited to a residue of a PEG-ester made from the polycondensation reaction of polyethylene glycol and a compound bearing multiple carboxylic groups, wherein the carboxylic group containing compounds include but are not limited to diglycolic acid, malonic acid, succinic acid, glutaric acid, adipic acid, tartaric acid, and carboxylic acid terminated-polyalkyleneglycols.

Examples of a PEG-ester version of $R_2$ residue include but are not limited to:

(a)

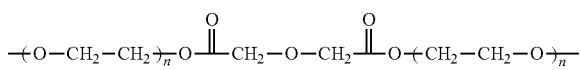

where n is 20 for PEG of Mw 900 and the diacid is diglycolic acid (b)

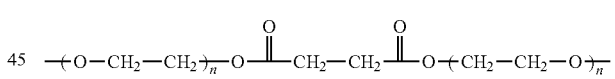

where n is 20 for PEG of Mw 900 and the diacid is succinic acid (c)

where n is 20 for PEG of Mw 900 and the diacid is glutaric acid (d)

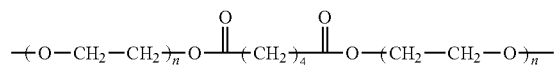

where n is 20 for PEG of Mw 900 and the diacid is adipic acid

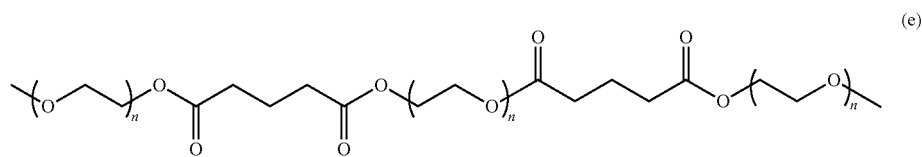
(e)
Other examples include branched $R_2$ residues are shown below:
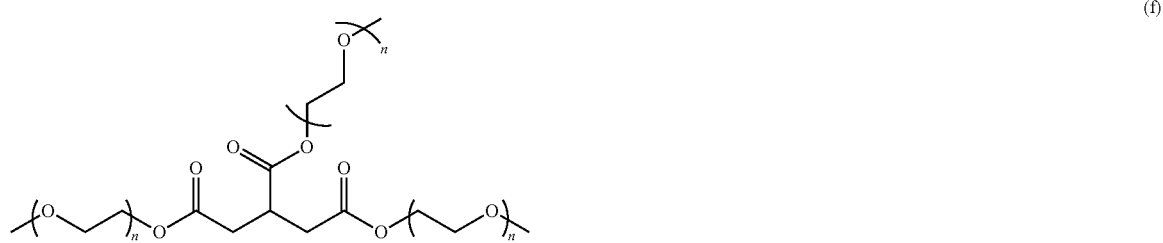
(f)
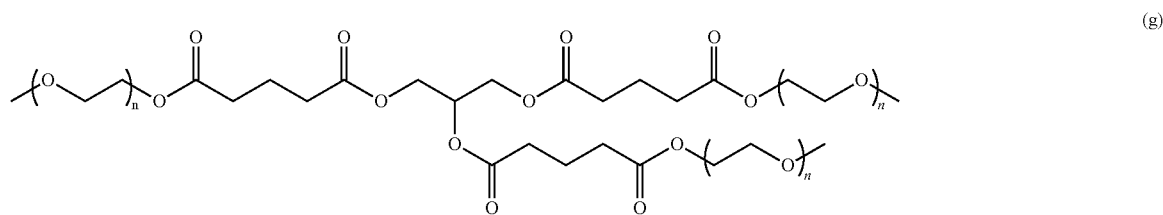
(g)
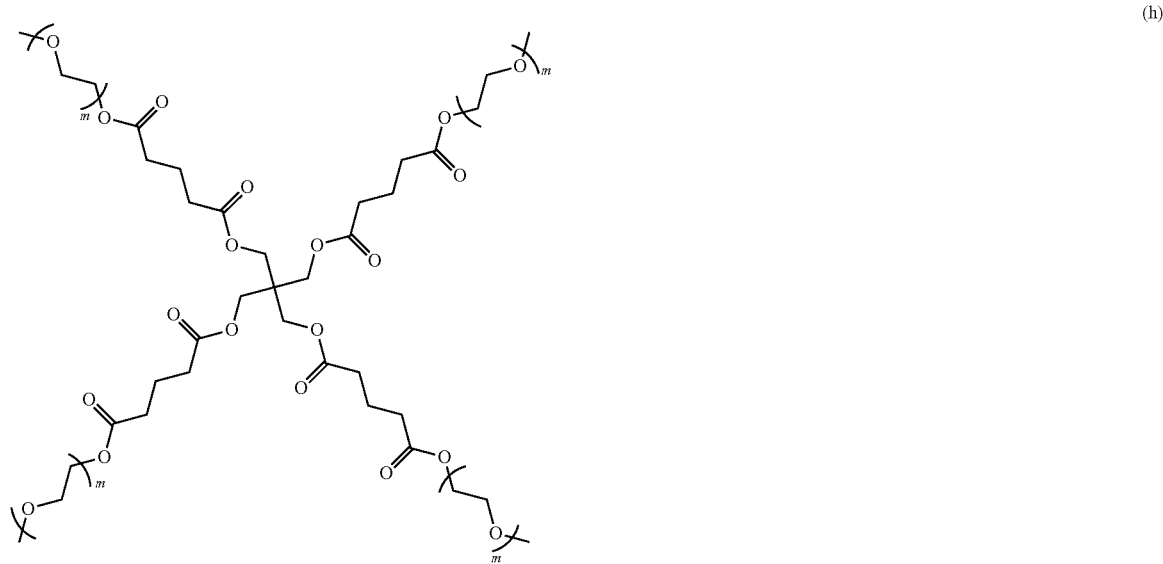
(h)
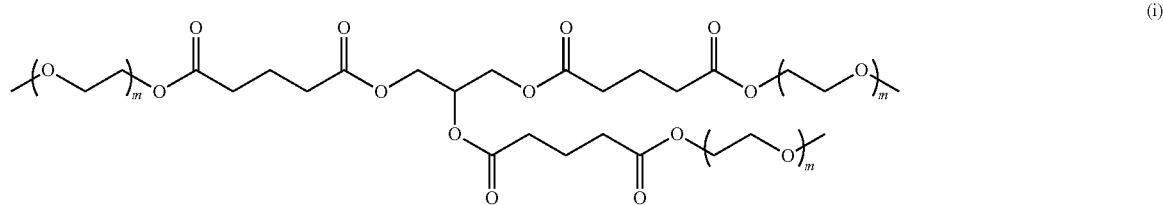
(i)

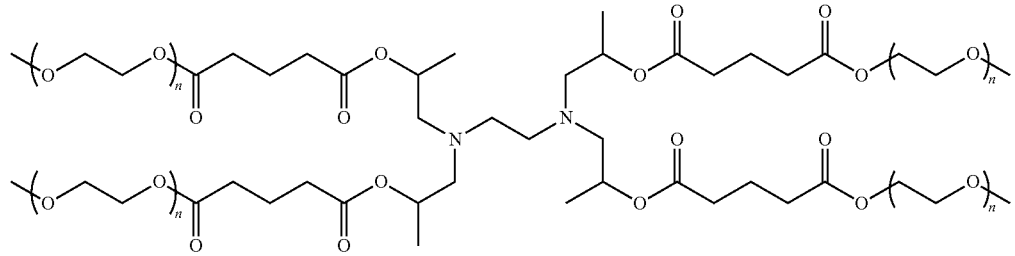
(j)

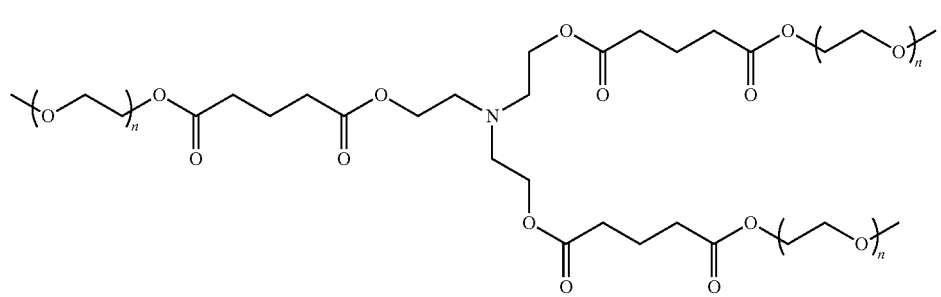
(k)

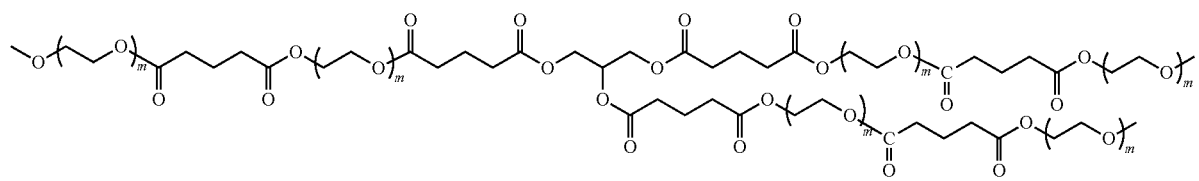
(l)

Figure 2:
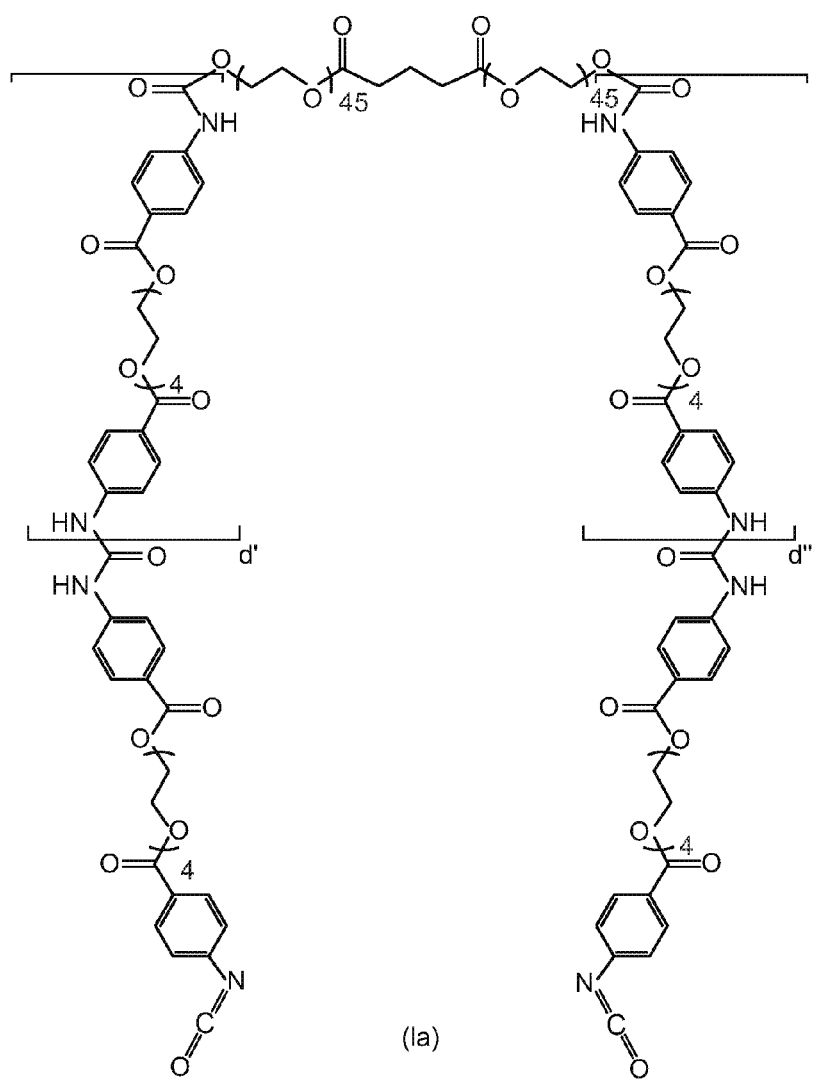
FIG. 2 shows an example of a linear macromer as Formula Ia.
Figure 3:
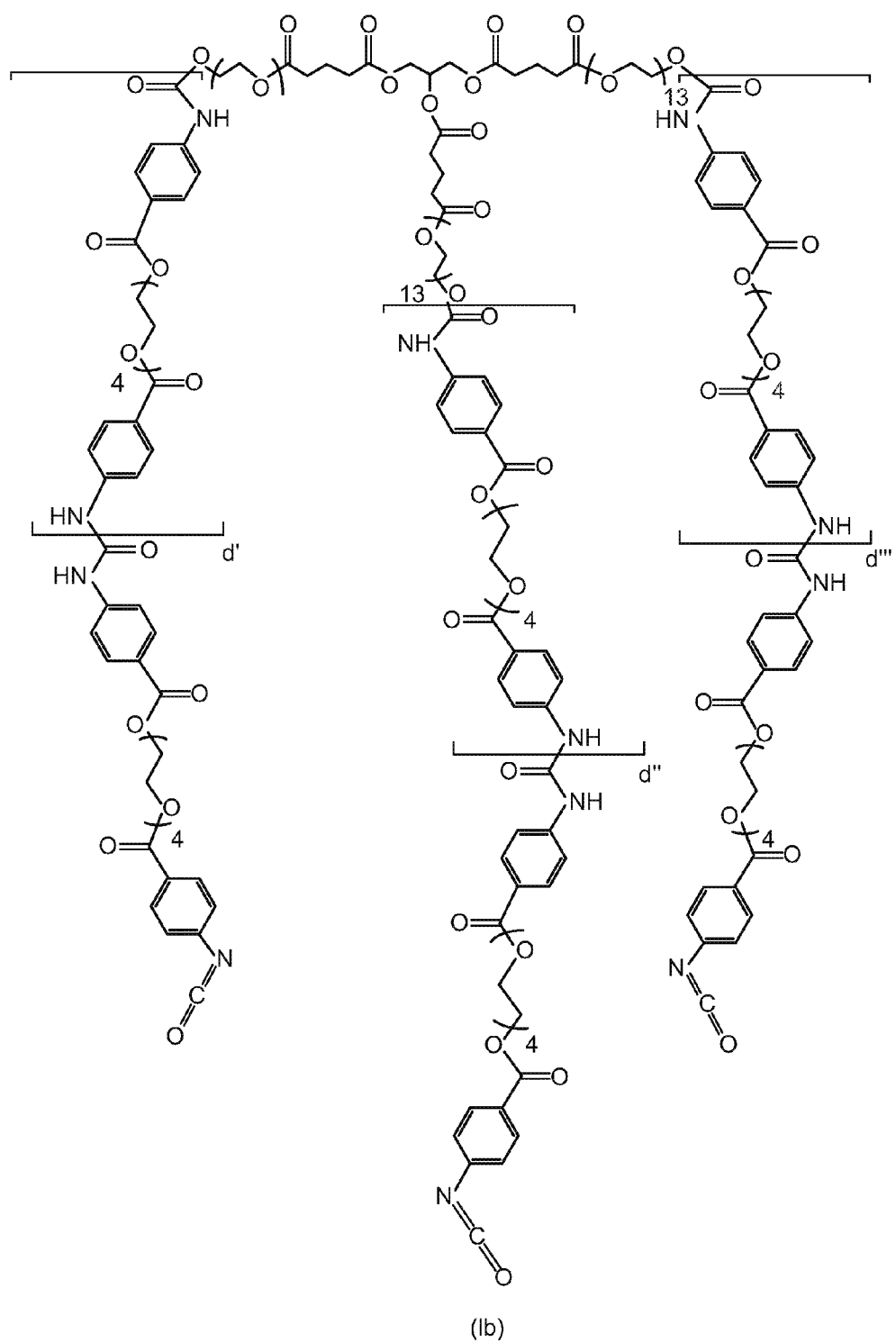
FIG. 3 shows an example of a branched macromer as Formula Ib.
Figure 4:
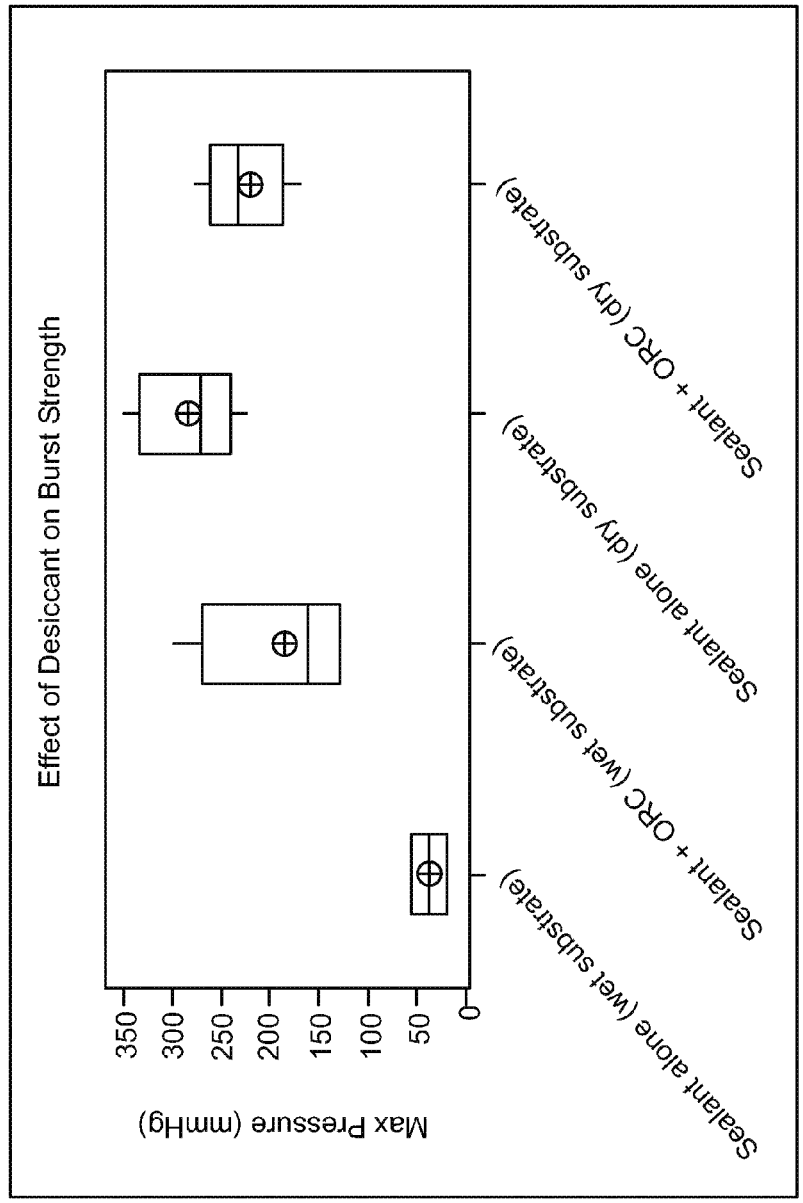
FIG. 4 depicts the improved burst strength achieved with the present formulation.

The molecular weight of the $R_2$ residue portion of the macromer may range from about 80 to 20,000 g/mol. An Example of a linear macromer is shown as Formula Ia (FIG. 2). An Example of a branched macromer is shown as Formula Ib (FIG. 3).

Producing a polyester polyol from which $R_2$ may be derived in high yield requires the use of a transition metal catalyst such as tin (II). Tin salts are well known as catalysts for esterification. They are hydrolytically stable and can withstand moisture generated during esterification without any loss of activity. They are more desirable to use than acid catalysts such as p-toluenesulfonic acid or mineral acids because these materials promote ether cleavage as well as oxidation, especially at higher temperatures. Typical temperatures during esterification of the polyols and polyacids range from 160-220° C. It is desirable to obtain a polyester polyol that contains as little oxidation side products as possible as this will affect the performance of the macromer. Tin catalysts also significantly reduce reaction times. Typical times to reach the desired polymer molecular weight and acid content range from 12-18 hours. To achieve a similar product without catalyst would require more than 60 hours. However, tin metal is toxic and must be removed from the polyol once esterification is complete.

Removing the tin catalyst after the reaction is completed poses a unique problem because regular methods to remove the catalyst are not as effective in polyester polyols. A common method is to use a small amount of hydrogen peroxide to oxidize the tin to an insoluble tin oxide, which can be filtered off. This is undesirable as treating any polyethylene glycol containing material with a peroxide will accelerate the formation of carbonyl and peroxide groups, which are undesirable impurities. Washing the material with water does not work either because the material itself is hydrophilic and tin is not easily hydrated. Adding a mineral acid to neutralize the tin is undesirable, as it will also hydrolyze eater bonds in the polymer. It is therefore desirable to find a mild adsorption agent that will selectively remove tin.

Citric acid can be used to chelate the tin catalyst, followed by treatment with silica to adsorb the tin citrate complex. Preferably a mixture of citric acid and silica is used. More preferably, a silica hydrogel treated with citric acid sold under the trademark Sorbsil R® by Ineos Silicas is used in the edible oils industry to remove trace metals and other polar impurities. The material is described as a silica hydrogel that is treated with citric acid. Citric acid is a known chelating agent and when covalently bound to silica, it increases the effectiveness of chelating metals such as tin compounds that are not as easily hydrated. Additionally, the polyester polyols have a high affinity for the tin catalyst since concentrations as high as 700 ppm of tin in the polymer are clear and free of sediment, which is not typical. Quantities from 0.01-1.00% by weight of oil can be used to effectively remove undesired impurities in the oil. This silica/citric acid mixture is suitable for removal of tin II & IV, both of which are common catalysts used in esterification. By treating a crude tin catalyzed polyester polyol with silica/citric acid, the tin can be adsorbed and filtered off leaving the metal free polyol. An organic solvent, such as toluene is necessary to aid in filtration because the silica/citric acid/tin complex is partially soluble in the polyester polyol. Since the silica/citric acid mixture is hydrophilic, it is necessary to add a hydrophobic solvent that will solubilize the polyester polyol and precipitate the silica-citric acid hydrogel. The hydrophobic solvents include, but not limited to, benzene, toluene, xylene, methylene chloride and chloroform. Addition of the solvent precipitates the complex facilitating filtration. Other materials, such as carbon powder and diatomaceous earth can be added during treatment to improve color and filtration times. Use of this method of tin removal results in a polyester polyol free of tin with no significant increase in acid content, which is a sign of hydrolysis. Typical polymers worked up in this manner have contained less than 5 ppm of tin (600 ppm tin before treatment), ~99.5% conversion of acid groups to ester groups (~99.8% conversion before treatment) and no significant evidence of carbonyl groups when analyzed by proton NMR.

For instance, a crude polyester polyol is treated with 1-10% by weight of a silicate, 0.05-1.00% by weight of carbon and 0-1% by weight of diatomaceous earth. The slurry is stirred for 30-90 minutes under an inert atmosphere at 60-85° C. The polymer is diluted to 40-60% by weight using a suitable organic solvent then filtered. The solvent is evaporated to yield the desired polyester polyol with low tin.

An alternative type of branched macromer is shown below as formula III. These are prepared by coupling an excess of linear isocyanate-terminated macromers of formula I with a multifunctional active hydrogen-terminated compound, such as a hydroxy-terminated compound, as shown here in $R_6$:

TABLE 1

Desirable Property Ranges for Intended Use of the Composition

| Property | Range | Preferred Range for Sealant | Preferred Range for Adhesive |
|---|---|---|---|
| elasticity[1] | 10-2000% | 50-500% | 10-50% |
| adhesive strength[2] | burst pressure: >200 mmHg | >200 mmHg | lap shear tensile strength >1 Mpa |
| cohesive strength[3] | 0.1-30 Mpa | 0.1-5 Mpa | 5-25 Mpa |

[2]Adhesive strength quantifies the ability of the adhesive/sealant material to adhere to the biological tissue. It is measured by the fluid burst pressure test-ASTM 2392-04 - Burst pressure testing is performed by cutting a linear incision of 0.5 cm in a substrate (pericardium, dura or collagen) and placing the substrate in a test fixture. Sealant is applied to the incision and allowed to cure. Increasing pressure is applied to the transverse side of the substrate using a syringe pump filled with fluid. The maximum pressure is recorded when the sealant ruptures.
[1, 3]Cohesive strength refers to the intrinsic ability of adhesive/sealant material to withstand tensile forces. Cohesive strength and elasticity are measured by Elongation and Modulus - Tensile specimens of cured sealant are prepared by casting as a film. The samples are tested in tension at 1 inch/minute until failure. The maximum load and elongation at failure are recorded.

The range of the molecular weight of the macromers described herein may be between about 500 to 20,000 g/mol, and preferably between about 500 and about 4000 g/mol.

Macromer-Containing Formulation:

A medically acceptable formulation may comprise the polyisocyanate macromer, a solvent, a catalyst, a surfactant, a stabilizer or antioxidant, and a color additive.

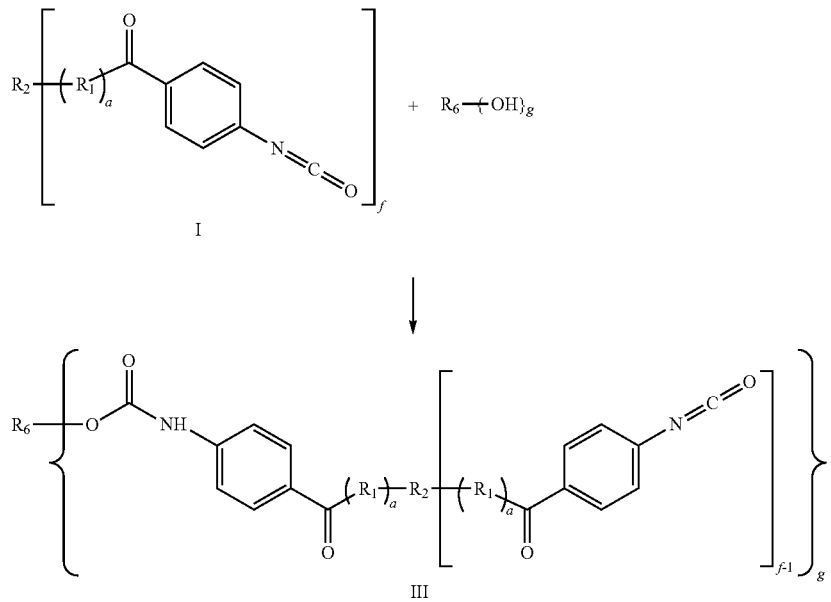

Wherein the intermediate polyol has g+1 hydroxyl end groups.

The molecular weight and degree of branching of the macromer are an important factors for determining biomechanical properties, such as elasticity, adhesive and cohesive strength, viscosity, absorption and water-uptake (swelling).

Typically, the solvent is a hydrophilic solvent, including but not limited to dimethyl sulfoxide (DMSO), acetone, dimethoxy PEGs, glycerine, Tween 80, dimethylisosorbide, propylene carbonate, and 1-methyl-2-pyrrolidinone (NMP). Less hydrophilic solvents may also be considered, such as: ethyl lactate, triacetin, benzyl alcohol, benzylbenzoate, various ester solvents, such as: triethyl citrate, acetyltriethyl citrate, tri-n-butyl citrate, acetyltri-n-butyl citrate, ethyl acetate and the like. For example, the solvent may be used in an amount up to about 50 weight % based on the total weight of solvent and macromer.

The solvent plays several roles in the macromer formulation: (1) viscosity control, (2) control of bubble/foam formation and bubble escape, (3) to enhance tissue penetration, and (4) to provide improved tissue wetting. The viscosity of the formulation ranges from 10 to 100,000 cp, preferably from 500 to 50,000 cp.

Additionally, it is desirable to incorporate from about 10 to 20 weight % of an absorbable desiccant such as oxidized regenerated cellulose in the macromer containing formulation in order to improve the adhesive strength of the resultant polymer that is formed upon polymerization of the polyisocyanate macromer. To reduce the impact of the absorbable desiccant on the ease of application of the macromer containing formulation, it is recommended to maintain the size of the desiccant particles/fibers as small as possible, ranging from about 0.1 to 1.3 mm. The oxidized regenerated cellulose includes but is not limited to Interceed® absorbable adhesion barrier, Surgicel® absorbable hemostat; Surgicel Nu-Knit® absorbable hemostat; and Surgicel® Fibrillar absorbable hemostat; each available from Johnson & Johnson Wound Management Worldwide or Gynecare Worldwide, each a division of Ethicon, Inc., Somerville, N.J. Specifically, it is believed that the absorbable desiccant helps the resultant polymer to improve its adhesive strength.

Surfactants may also be added to the formulation to control foaming: non-ionic surfactants such as Tween, Brij and siloxanes, as well as ionic surfactants, such as lecithin (phosphatidyl choline), sodium dodecyl sulfate, among others known in the arts.

Catalysts may also be added to the formulation for to increase reaction speed, such as triethylene diamine (DABCO), pyridine, ethyl-2-pyridyl acetate, and stannous octoate.

The color additive that may be utilized in the macromer formulation includes, but is not limited to, methylene blue, FD&C Blue #1 or #2, and conventional color additives that are used in absorbable medical devices such as sutures.

Antioxidants such as butylated hydroxyl toluene (BHT) may be present in the macromer formulation to improve shelf stability of the product.

Adhesive System

One example of an adhesive system includes, but is not limited to, a system where the macromer and a solvent are stored separately until ready for use. For example, the macromer may be stored in one barrel of a double barrel syringe while the solvent is stored in the other barrel. Alternatively, the macromer and the solvent may be mixed by any conventionally means prior to use.

Biocompatible Elastic Gel

The resultant polymer after the in vivo polymerization of the macromer is an elastic gel that is biodegradable, and the degradation products thereof should be both biocompatible and water soluble, so that the degradation products are completely eliminated from the human body as waste products.

Specifically, the macromer or formulation thereof polymerizes to form a biocompatible elastic gel upon contact with water or body fluids, via the following reaction scheme:

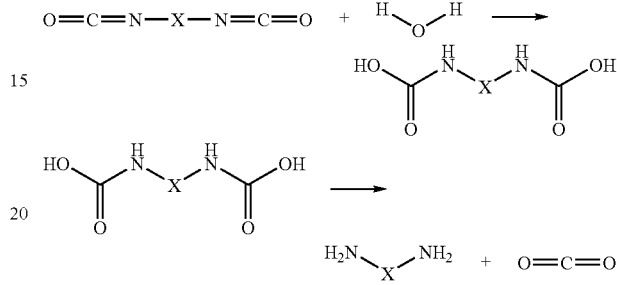

wherein X represent the structural component between the two terminal functional groups and X depends on the type of macromer utilized. The above reaction readily occurs under body conditions resulting in the spontaneous degradation of the dicarbamate to the diamine and carbon dioxide.

In a subsequent reaction, the newly formed diamine reacts with and isocyanate group to form an elastic gel, via the following reaction scheme:

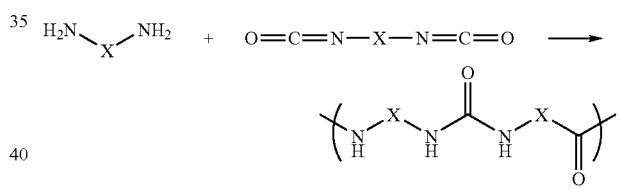

Degradation Products

The elastic gel formed from the macromer described herein is biodegradable and degrades by hydrolysis in vivo to form degradation products, including aromatic degradation products, that are both biocompatible and water soluble. In order to insure water solubility of any aromatic degradation product, the elastic gel is designed to cleave in such a way that the terminal groups on the aromatic degradation product are residues of water-soluble polymers. For example, after the macromer adhesive or sealant formulation polymerizes in the body, the elastic gel that results has the following repeat unit as shown in formula IV.

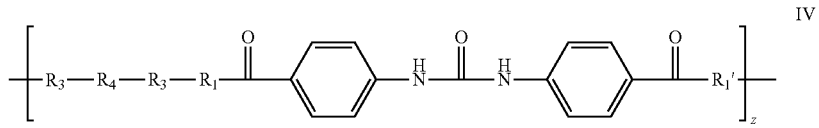

The biocompatible elastic gel (IV) that is formed comprises various hydrolysable linkages, including but not limited to, aliphatic and aromatic ester linkages, urethane linkages and urea linkages. The aliphatic ester linkages in the elastic gel have a higher tendency to degrade in vivo, than the other types of linkages, thereby leaving an initial aromatic degradation product V.

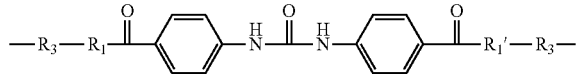

V

While there are other linkages in the aromatic degradation product V fragment that are susceptible to hydrolytic degradation (e.g., urethanes, and aromatic esters), for all practical purposes these do not degrade in vivo to any significant extent before the aromatic degradation product is excreted from the body. For example, the rapidly hydrolysable aliphatic ester linkages between $R_3$ and $R_4$, in the elastic gel degrade within 0-6 months; the more slowly hydrolysable aromatic ester linkages in the aromatic degradation product degrade within 4-24 months; the urethane linkages in the aromatic degradation product degrade within 4 to 24 months; and the very slowly hydrolysable urea linkages in the aromatic degradation product degrade within 24 month to infinity. During the timeframe from implantation of the macromer adhesive or sealant formulation to excretion of the aromatic degradation product V from the body, degradation of the aromatic ester, urethane and urea linkages in the aromatic degradation product V do not occur to any significant extent.

This composition has multiple medical applications. For example, as an internal surgical adhesive, the adhesive can bond tissue to tissue, tissue to medical device and medical device to medical device. As a sealant, the composition can be coated on a tissue, or on a medical device, or on the interface of a medical device with tissue to prevent leaks. The composition can be used to form films in situ that may have applications such as for the prevention of surgical adhesions. The composition can be used to form foams in situ that may have applications such as a filler (e.g. dead space removal, reconstructive and cosmetic surgeries), bulking agents, tissue engineering (e.g. scaffolds) materials and others where foams and sponges are useful. The composition can be formulated so that it is injectable and used to form gels in situ that are localized, and adherent to tissue, staying at the site where they are injected. These may have applications such as a delivery matrix for cells and other biologicals, bioactive agents and pharmaceutical or neutraceutical agents, and as embolization agents, and as means to localize contrasting agents. The composition may also be used to attach medical devices (e.g. meshes, clips and films) to tissues. This composition can be used internally in many types of surgery, including, but not limited to, cardiovascular, peripheral-vascular, cardio-thoracic, gynecological, neuro- and general abdominal surgery.

As a surgical sealant/adhesive, it can be used as an adjunct to primary wound closure devices, such as staples, sutures, to seal potential leaks of gasses, liquids, or solids. More specifically, the surgical adhesive/sealant may be applied to a tissue as a part of a surgical procedure, in various forms, for example: liquid, powder, film, sponge or foam, impregnated fabric, impregnated sponge or foam, or spray.

As a filler, the macromer or formulation thereof may be used as a facial, defect or void filler. For example, the formulation may be applied in the interstices of an internal void and allowed to polymerize therein, such that the polymer fills the internal cavities and voids, penetrating and conforming to the interstices and pores of the tissue. The formulation may be used after a broad number of procedures having potential risk of dead space formation, including, but not limited to, radical mastectomy (i.e. breast and regional lymph nodes removal for cancer treatment), breast reconstruction and augmentation procedure, reconstructive or cosmetic abdominoplasty and liposuction, face-lift, cesarean section and hysterectomy in obese patients, orthopedic procedures on thigh region, incisional hernia repair, lipoma excision, and traumatic lesions, i.e. closed trauma.

While the following examples demonstrate certain embodiments of the invention, they are not to be interpreted as limiting the scope of the invention, but rather as contributing to a complete description of the invention.

EXAMPLE 1

Part A: Preparation of Isocyanate Macromer Id (FIG. 1)

To a clean, dry 250 mL 3 neck flask fitted with nitrogen inlet, temperature probe and dean-stark trap was charged 8.72 g (0.0947 moles) of Glycerin USP. The contents were heated to 120° C. with stirring under nitrogen. Upon reaching temperature, vacuum was applied for 2 hours. Vacuum was released and 32.46 g (0.2845 moles) of Glutaric Anhydride was added. The solution was stirred under nitrogen at 120° C. for 2 hours until IR showed no anhydride present. The solution was cooled and 167.09 g (0.2784 moles) of PEG 600 NF and 0.20 g (0.0009 moles) of Tin (II) Oxalate were added. The flask was heated to 180° C. and held for 2 hours under nitrogen sparge. Vacuum was applied for an additional 17 hours after which the conversion of acid to ester groups was 99.98% based on the acid content. The polyol was cooled to 80° C. and the following were added; 6.13 g of silica-citric acid and 2.38 g of diatomaceous earth. The slurry was stirred at 80° C. under nitrogen blanket for 1 hour. The slurry was diluted to 50% w/v in toluene and stirred for another 15 minutes and filtered through 2-micron cellulose paper. The solvent was evaporated to leave a pale yellow, viscous liquid. Yield=91%, ester conversion=99.73%, Tin content=less than 5 ppm.

Part B:Preparation of Macromer Ic (FIG. 2)

To a clean, dry 1 L 4-neck flask fitted with mechanical stirrer, nitrogen inlet, temperature probe and dean-stark trap was charged 149.79 g (0.3744 moles) of PEG 400 NF. The contents were heated to 120° C. with stirring under nitrogen. Upon reaching temperature, vacuum was applied for 1.5 hours. Vacuum was released and 85.56 g (0.7499 moles) of Glutaric Anhydride was added. The solution was stirred under nitrogen at 120° C. for 2.5 hours until IR showed no anhydride present. The solution was cooled and 436.06 g (0.7268 moles) of PEG 600 NF and 0.67 g (0.0032 moles) of Tin (II) Oxalate were added. The flask was heated to 180° C. and held for 2 hours under nitrogen sparge. Vacuum was applied for an additional 16 hours after which the conversion of acid to ester groups was 99.96% based on the acid content. The polyol was cooled to 80° C. and the following were added; 6.97 g of silica-citric acid, 7.11 g of diatomaceous earth and 3.39 g of activated carbon. The slurry was stirred at 80° C. under nitrogen blanket for 1 hour. The slurry was diluted to 50% w/v in toluene and stirred for another 15 minutes and filtered through 2-micron cellulose paper. The solvent was evaporated to leave a pale yellow, viscous liquid. Yield=95%, ester conversion=99.88%, Tin content=less than 5 ppm.

Part C: Preparation of Macromer Mixture of Ic: and Id (in a 1:1 Ratio)

To a clean, oven dried 2 neck 250 mL flask fitted with a mechanical stirrer was charged 28.18 g (0.0154 moles) of the Polyester Polyol described in example 1B and 33.90 g (0.0152 moles) of the Polyester Polyol described in example 1A. The polyol mix was dried under vacuum on a 120° C. oil bath with stirring for 8 hours. The dried polyol was cooled and 59.38 g (0.0.1224 moles) of Prepolymer B1 from example 2 was added under a nitrogen atmosphere. The mixture was stirred for 20 hours under nitrogen at 70° C. The prepolymer was cooled and diluted to 75% solids in Acetone to yield a viscous amber liquid with a viscosity of ~12,000 cst (25° C.).

EXAMPLE 2

15 wt % of SURGICEL* Fibrillar absorbable hemostat was mixed with the macromer mixture described in Part C by stirring the absorbable desiccant in the unreacted macromer mixture. This formulation was applied on a hydrated collagen substrate with and without free water present (addition 10 μl saline). The average burst pressures were 185 mmHg and 226 mmHg, respectively. By comparison, the macromer mixture described in Part C alone was applied on a hydrated collagen substrate with and without free water present (addition 10 μl saline), and the average burst pressures were 37 mmHg and 279 mmHg, respectively. It is believed the absorbable desiccant serves to improve the adhesion of the polymer to a substrate when excess free water at a surgical site limits the effectiveness of the adhesive.

What is claimed:

1. A medically acceptable liquid formulation comprising (i) a polyisocyanate macromer or mixture of macromers of the following formula (ii) and from about 10% to 20% by weight of an oxidized cellulose in particle form having a size of less than 1.3 mm

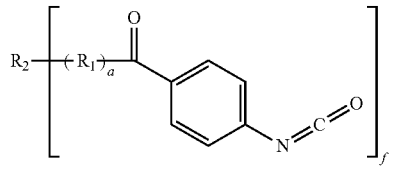

wherein f is two or more; "a" is one to five and $R_1$ is

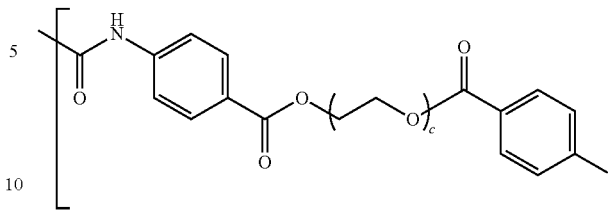

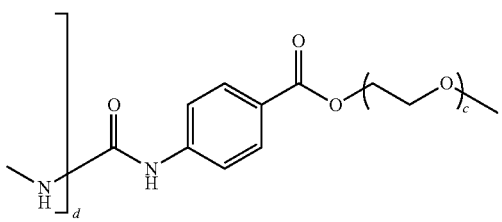

where the ethylene oxide portion of $R_1$ is linear or branched, d is a real number ranging from 0 to 5 and c ranges from 1 to 100; $R_2$ is

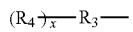

where $R_3$ is a linear or branched residue of a water soluble polymer that forms ester linkages to $R_4$, and urethane linkages to $R_1$ when "a" is one to five; and $R_4$ is a linear or branched organic residue having "x" carboxylate end-groups where $2 \leq x \leq 6$.

2. The medically acceptable formulation of claim 1, where f is two, and the macromer is represented by the formula:

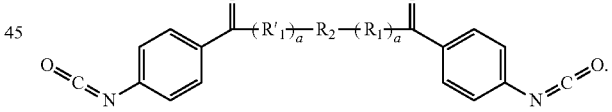

3. The medically acceptable formulation of claim 2, where $R_1'$ is represented by the formula:

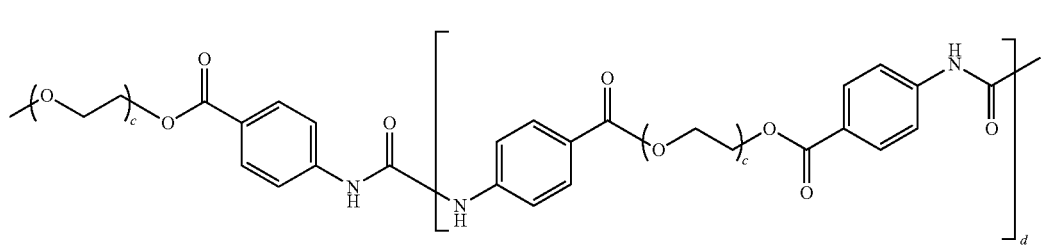

4. The medically acceptable formulation of claim 1, where $R_2$ is selected from the group consisting of
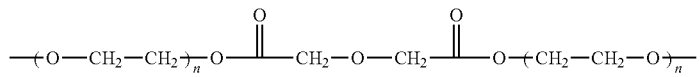
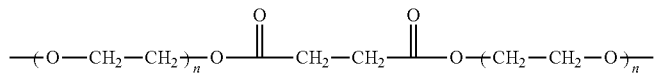
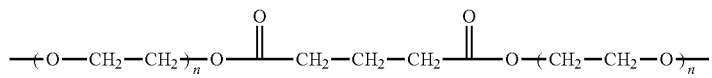
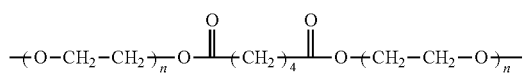
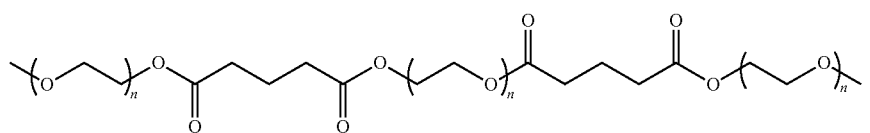
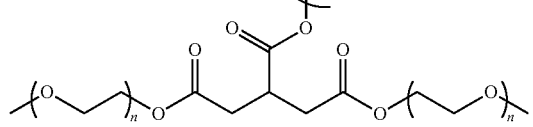
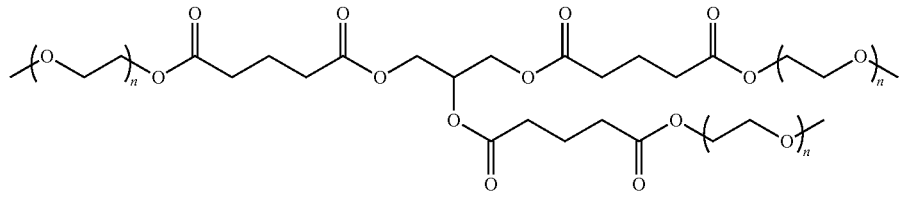
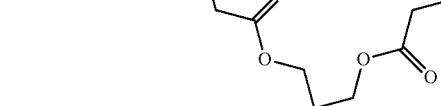
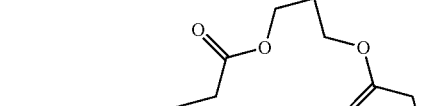

-continued

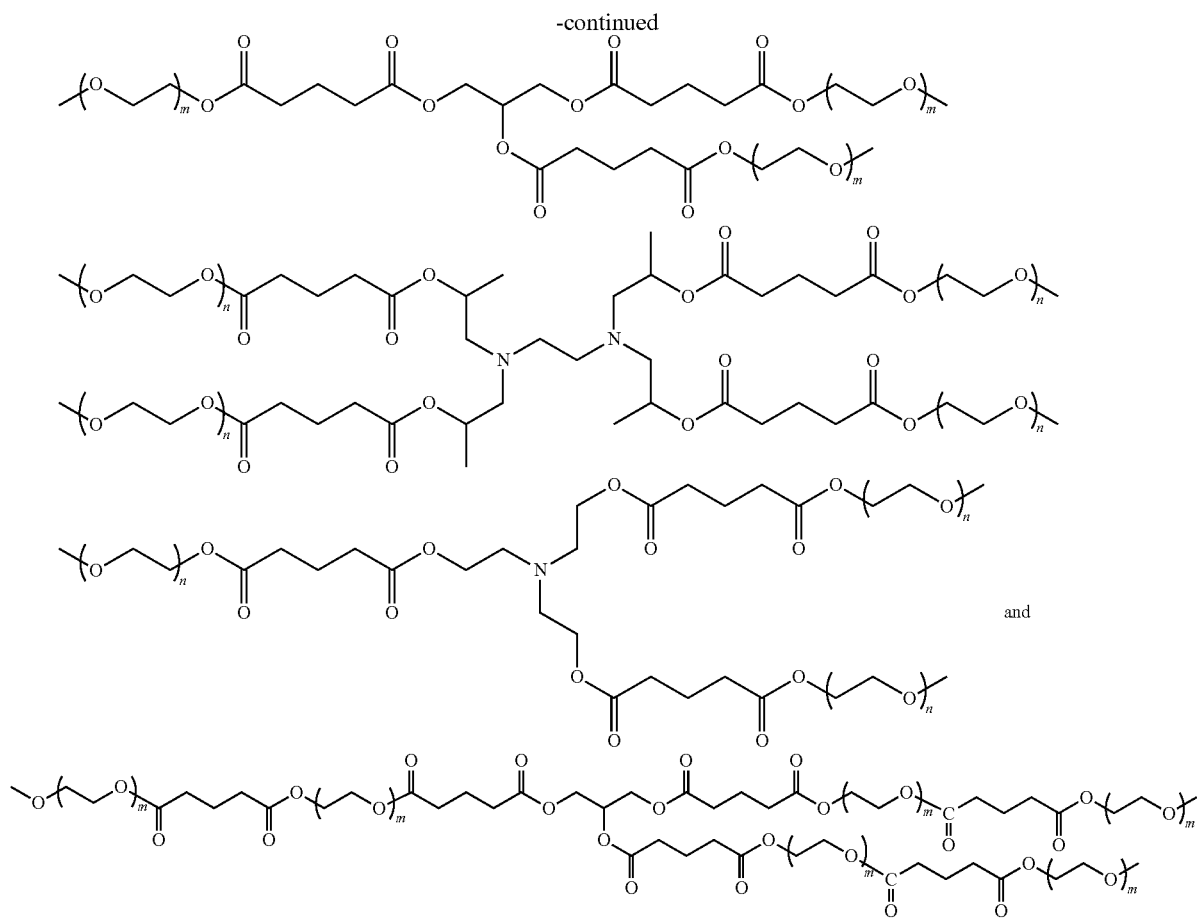

where n is from 2 to 250 and m is from 1 to 10.

5. The medically acceptable formulation of claim 1, where $R_3$ is a residue of a compound selected from the group consisting of a polyalkylene glycol, a polyalkylene oxide, polyvinylpyrrolidone, poly(vinyl alcohol), poly(vinyl methyl ether), polyhydroxymethyl methacrylate, a polyacrylic acid polymer and copolymer, polyoxazoline, polyphosphazine, polyacrylamide, a polypeptide, and water soluble derivative thereof; and R4 is a residue of a compound selected from the group consisting of diglycolic acid, malonic acid, succinic acid, glutaric acid, adipic acid, tartaric acid, citric acid, tricarballylic acid, glycerol triglutarate, pentaerythritol tetra glutarate, and erythritol.

6. The medically acceptable formulation of claim 1, where the oxidized cellulose is an absorbable desiccant.

* * * * *